United States Patent
Battles

(10) Patent No.: US 8,328,717 B2
(45) Date of Patent: Dec. 11, 2012

(54) SEAL DEVICE WITH ADJUSTABLE APERTURE

(75) Inventor: Christopher A. Battles, Seymour, CT (US)

(73) Assignee: Covidien LP, Mansfield, MA (US)

( * ) Notice: Subject to any disclaimer, the term of this patent is extended or adjusted under 35 U.S.C. 154(b) by 274 days.

(21) Appl. No.: 12/714,823

(22) Filed: Mar. 1, 2010

(65) Prior Publication Data
US 2010/0249522 A1  Sep. 30, 2010

Related U.S. Application Data

(60) Provisional application No. 61/164,094, filed on Mar. 27, 2009.

(51) Int. Cl.
*A61B 1/32* (2006.01)
(52) U.S. Cl. .................. 600/206; 600/208; 604/167.06
(58) Field of Classification Search ............ 604/164.01, 604/264, 167.01–167.06, 256, 30; 606/167, 606/185; 600/204–210
See application file for complete search history.

(56) References Cited

U.S. PATENT DOCUMENTS

| | | | |
|---|---|---|---|
| 4,183,357 A | 1/1980 | Bentley et al. | |
| 5,366,478 A | 11/1994 | Brinkerhoff et al. | |
| 5,389,081 A * | 2/1995 | Castro | 604/167.03 |
| 5,391,156 A | 2/1995 | Hildwein et al. | |
| 5,407,433 A * | 4/1995 | Loomas | 604/167.06 |
| 5,507,758 A | 4/1996 | Thomason et al. | |
| 5,603,702 A * | 2/1997 | Smith et al. | 604/256 |
| 5,634,911 A | 6/1997 | Hermann et al. | |
| 5,683,378 A | 11/1997 | Christy | |
| 5,906,577 A | 5/1999 | Beane et al. | |
| 5,964,781 A | 10/1999 | Mollenauer et al. | |
| 5,997,515 A | 12/1999 | de la Torre et al. | |
| 6,142,936 A | 11/2000 | Beane et al. | |
| 6,228,063 B1 | 5/2001 | Aboul-Hosn | |
| 6,238,373 B1 | 5/2001 | de la Torre et al. | |
| 6,382,211 B1 | 5/2002 | Crook | |
| 6,440,063 B1 | 8/2002 | Beane et al. | |
| 6,454,783 B1 | 9/2002 | Piskun | |
| 6,551,270 B1 | 4/2003 | Bimbo et al. | |
| 7,163,510 B2 | 1/2007 | Kahle et al. | |
| 7,223,257 B2 | 5/2007 | Shubayev et al. | |
| 7,344,547 B2 | 3/2008 | Piskun | |
| 7,473,221 B2 | 1/2009 | Ewers et al. | |
| 7,762,990 B2 * | 7/2010 | Judson et al. | 604/167.06 |
| 7,850,660 B2 * | 12/2010 | Uth et al. | 604/175 |
| 7,918,827 B2 * | 4/2011 | Smith | 604/167.06 |
| 2005/0020884 A1 | 1/2005 | Hart et al. | |
| 2008/0027476 A1 | 1/2008 | Piskun | |

FOREIGN PATENT DOCUMENTS

WO   WO 96/36283   11/1996

OTHER PUBLICATIONS

European Search Report for EP 10 25 0607 date of completion is Jun. 30, 2010 (3 pages).

* cited by examiner

*Primary Examiner* — Pedro Philogene

(57) ABSTRACT

A seal device comprising: a seal housing defining a central axis, the seal housing having an inner wall and an outer wall, the inner wall defining an opening along the central axis; a rotatable head mounted to the seal housing; at least one finger pivotally mounted to the rotatable head, the fingers defining an aperture for reception of a surgical instrument; and a cam mounted to the rotatable head for pivoting the fingers upon rotation of the rotatable head, the at least one finger configured to reduce the amount by which the surgical instrument may be moved off-axis relative to the central axis.

10 Claims, 3 Drawing Sheets

SEAL DEVICE WITH ADJUSTABLE APERTURE

CROSS REFERENCE TO RELATED APPLICATION

The present application claims the benefit of and priority to U.S. Provisional Application Ser. No. 61/164,094 filed on Mar. 27, 2009, the entire contents of which are incorporated herein by reference.

BACKGROUND

1. Technical Field

The present disclosure relates to an adjustable aperture seal system adapted to permit the introduction of surgical instrumentation into a patient's body.

2. Background of Related Art

Minimally invasive surgical procedures, such as laparoscopic surgery, result in reduced trauma for a patient than an equivalent open procedure. In this procedure, trocar assemblies including narrow hollow tubes called cannula are inserted into small incisions made into a patient's skin by a trocar. Elongated surgical instruments are inserted into the patient's body cavity through the cannula.

Often the patient's body cavity has been insufflated with carbon dioxide to separate the cavity wall from the internal organs therein. This creates a working and a viewing space. Therefore, a tight seal must be maintained between the body cavity and the outside environment.

Maintaining such a seal is complicated since it is often desirable to insert and remove several surgical instruments through one cannula in a single surgical procedure. While it is ideal to use the smallest available surgical instruments, some complex instruments may not be able to fit inside such a small cannula. The seal that is used must be sized to receive the instrument.

Ideally, a surgeon should be able to use one seal system to accommodate all the instruments used during the surgical procedure. The known seals are deficient in numerous ways, including an inability to accommodate instrumentation or various sizes and inability to preserve the integrity of the seal as instrumentation is manipulated. Accordingly, the current disclosure provides a seal device that resolves these shortcomings.

SUMMARY

The present disclosure describes a seal device adapted to permit the introduction and use of surgical instruments of various dimensions into a patient's body while maintaining a seal around the instruments. In one embodiment, a seal device is described in which the diameter of an aperture, through which surgical instruments are inserted, is adjustable by rotating a head coupled to a cam that pivots fingers defining the aperture. This allows the seal device to accommodate a range of instruments having a variety of tip configurations and a variety of diameters.

In a particular embodiment of the present invention, a seal device comprises a seal housing defining a central axis, the seal housing having an inner wall and an outer wall, the inner wall defining an opening along the central axis; a rotatable head mounted to the seal housing; at least one finger pivotally mounted to the rotatable head, the fingers defining an aperture for reception of a surgical instrument; and a cam mounted to the rotatable head for pivoting the fingers upon rotation of the rotatable head, the at least one finger configured to reduce the amount by which the surgical instrument may be moved off-axis relative to the central axis. The seal device may also include an instrument seal for substantially sealing about the surgical instrument, and a zero-closure seal for providing a substantial seal in the absence of a surgical instrument. The rotatable head may include indicia which provide an indication to a user of the appropriate size of an instrument that may be inserted therethrough. The indicia may include a window defined by the rotatable head through which numerical markings may be visible.

BRIEF DESCRIPTION OF THE DRAWINGS

By way of description only, embodiments of the disclosure will be described with reference to the accompanying drawings, in which:

FIG. 3b is a top view of a the seal device of FIG. 3a;

FIG. 4b is a top view of the seal device of FIG. 4a.

DETAILED DESCRIPTION OF THE EMBODIMENTS

Figure 2:
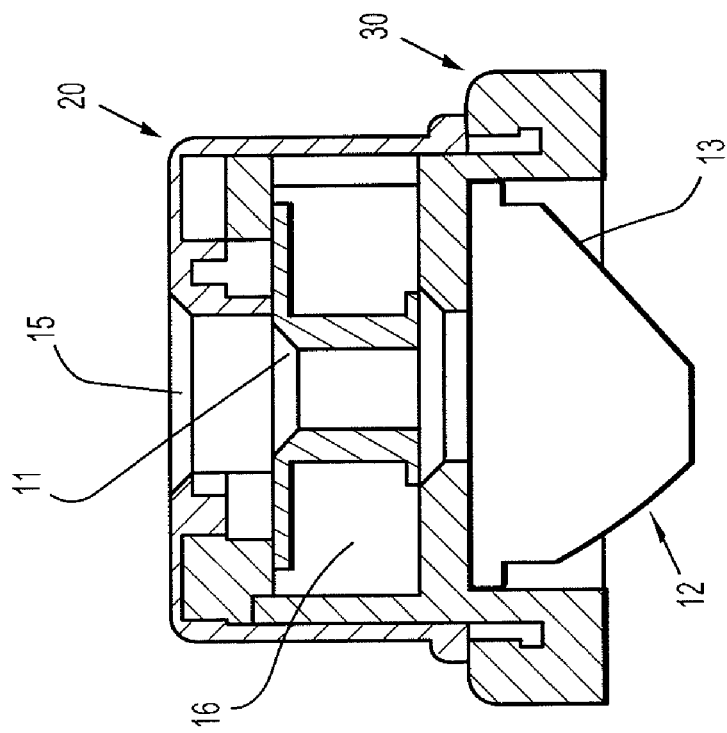
FIG. 2 is a side cross sectional view of the seal device of FIG. 1.

Particular embodiments of the present disclosure will be described herein with reference to the accompanying drawings. As shown in the drawings and as described throughout the following descriptions, and is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

A seal device 100 allows for the introduction and manipulation of a variety of instruments adapted for insertion through a trocar or cannula assembly while preserving the atmospheric integrity of the body cavity from gas or fluid leakage. Examples of instrumentation used in such procedures includes, but is not limited to, clip appliers, graspers, dissectors, retractors, staplers, laser probes, photogenic devices, endoscopes and laparoscopes, tubes and the like. Such instruments will be collectively referred to herein as "instruments or instrumentation".

The seal device 100 is adapted for use with a trocar assembly, including an obturator and a cannula, and is utilized for minimally invasive, such as endoscopic or laparoscopic procedures. The seal device 100 cooperates with the obturator or other instruments extending through the cannula to form a seal around the outer surface of the instrument and preclude the passage of fluids or gases through the body cavity and trocar assembly.

Figure 3B:
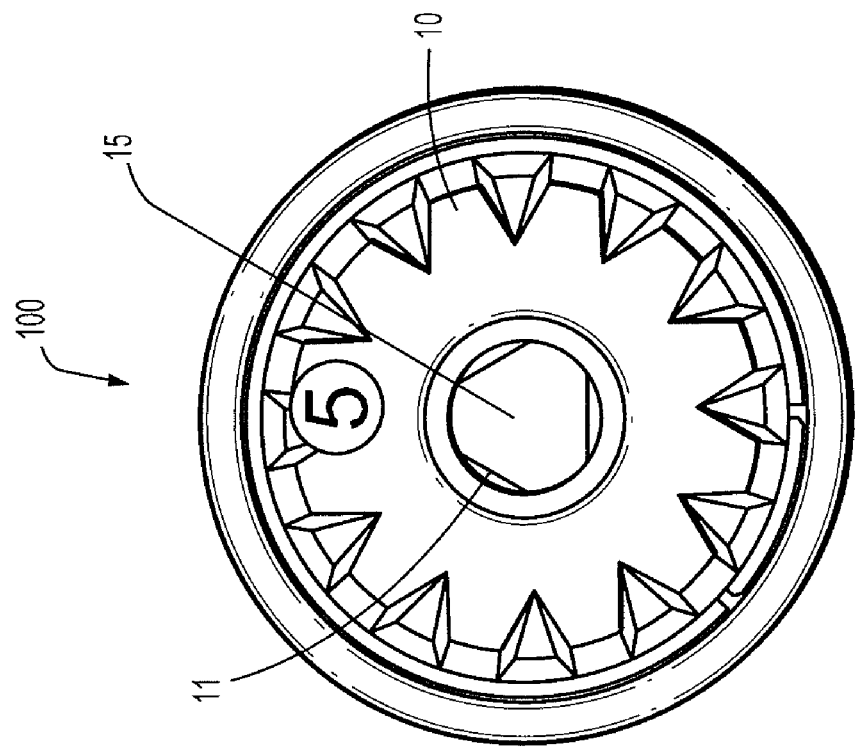
Figure 3A:
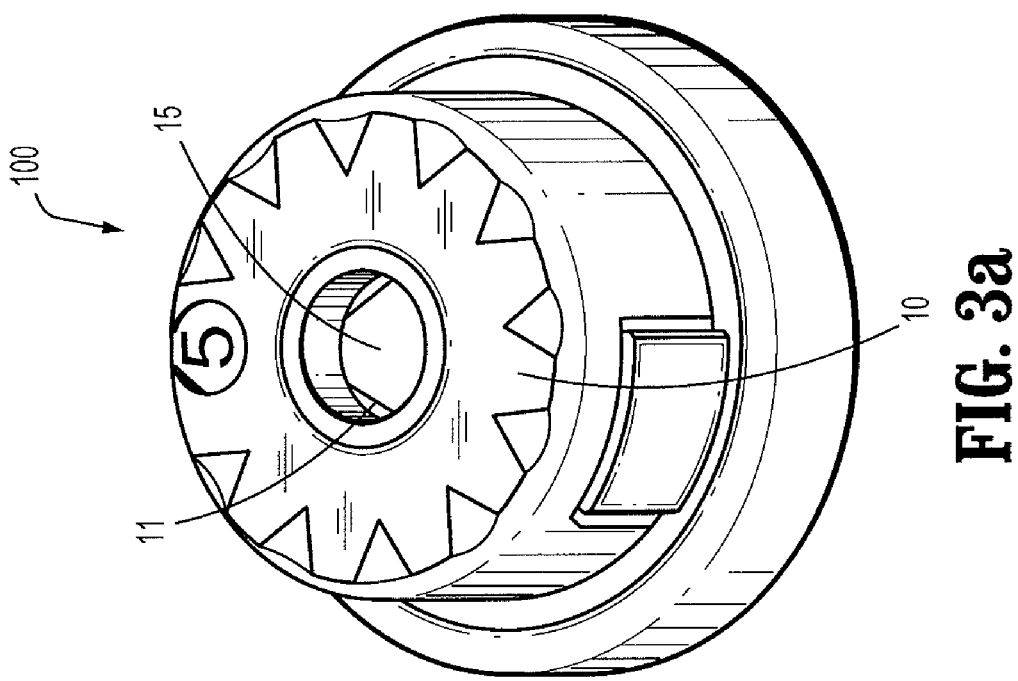
FIG. 3a is a perspective view of the seal device adjusted to form a first aperture.
Figure 4B:
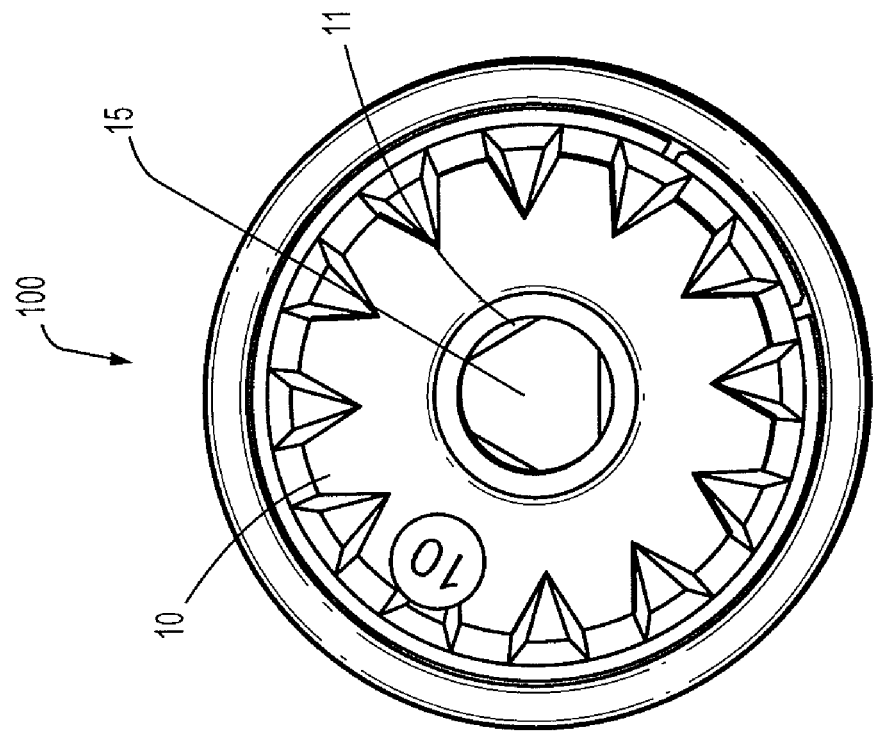
Figure 4A:
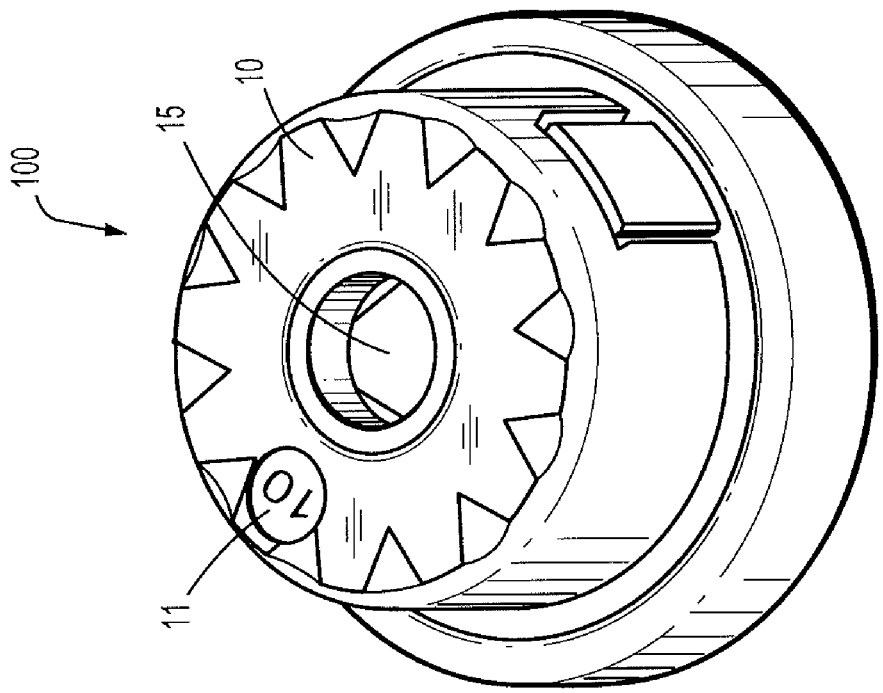
FIG. 4a is a perspective view of the seal device adjusted to form a second aperture.

In one embodiment, the seal device 100 includes an aperture 15 of variable diameter defined by the cam fingers 11. Aperture 15 allows for the passage of surgical instruments inserted therethrough. The seal device 100 can be described as having an inner housing 20 and an outer housing 30. The inner housing 20 has spaces formed therein to accommodate rotational movement of the cam 16 and the cam fingers 11. When a surgeon desires to adjust the diameter of aperture 15, rotatable head 10 is rotated. When rotated, the rotatable head 10 rotates a cam 16 which in turn pivots cam fingers 11. The cam fingers 11 collectively define aperture 15. By pivoting cam fingers 11, the surgeon may adjust the size of the aperture 15. FIGS. 3a-3b and FIGS. 4a-4b show the seal device 100 after the rotatable head has been positioned to define an aperture 15 of different diameters, e.g., 5 mm and 10 mm, respectively. The seal device 100 can also define numerous apertures between 5 mm and 20 mm, e.g., 7 mm, or any other size aperture.

Figure 1:
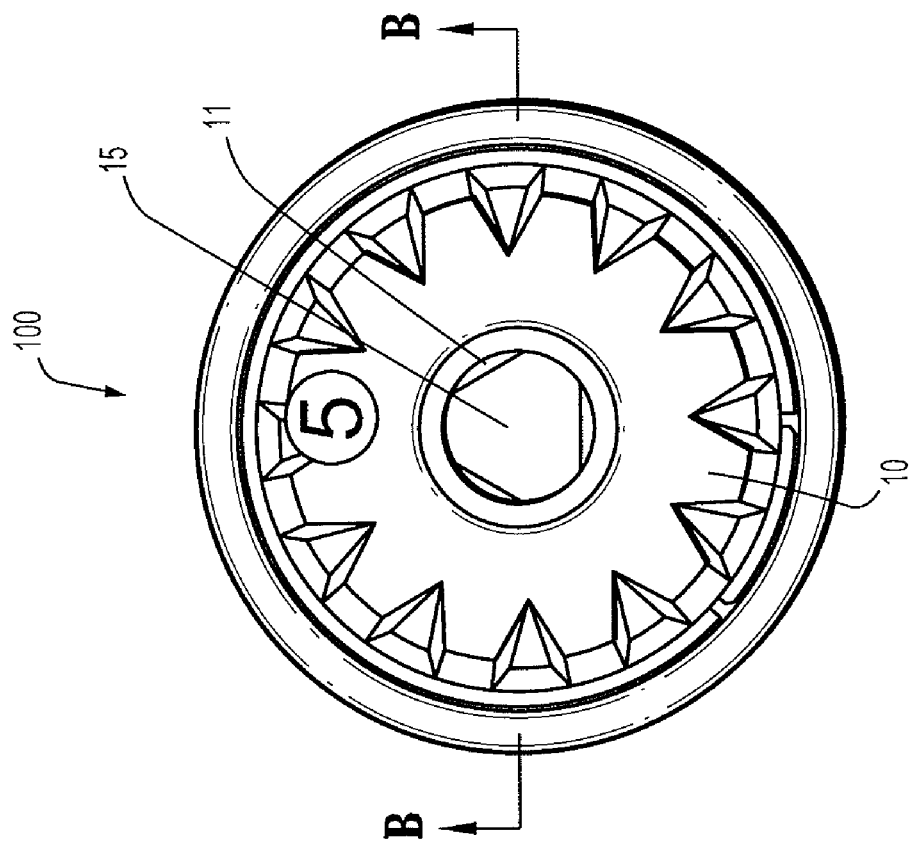
FIG. 1 is a top view of a seal device according to an embodiment of the present disclosure.

The rotatable head 10 may include indicia which provides an indication to a user of the appropriate size of an instrument that may be inserted therethrough. For example, the rotatable head 10 shown in FIGS. 1 through 4(b) defines a window through which numerical markings may be visible. In this manner, a user may be provided with an indication that the cam fingers are suitably positioned for insertion of e.g., a 5 mm instrument, a 10 mm instrument, etc.

Adjustment of the cam fingers 11 in this manner may help prevent seal leakage, since the cam fingers may help reduce the amount by which an instrument inserted and used therein may be moved off-axis. By reducing the amount by which an instrument may be moved off-axis, there may be a reduced likelihood that a gap will be formed between the instrument and the instrument seal 13.

In one embodiment, the seal device 100 has a proximal end and a distal end. The proximal end of the seal device 100 is adapted to receive an instrument. The distal end of the seal device is adapted to engage the trocar assembly. Beneath the distal end of the seal device are a zero-closure valve, e.g., duckbill seal 12 and an instrument seal 13. The instrument seal 13 is adapted to form a tight seal with the trocar assembly.

The duckbill seal 12 prevents fluid and/or gas leakage after an instrument is withdrawn from the seal device 100. In one embodiment, the duckbill seal 12 is a one-way elastomeric member that allows for the insertion of instrumentation while inhibiting fluid and gas leakage between the shaft of the instrument and the duckbill seal 12.

Cam fingers 11, duckbill seal 12, and instrument seal 13 may be made from a flexible and/or elastic material, such as a urethane, silicone, natural or synthetic rubber or other elastomeric material. The material may be resistant to tears and should be impervious to gases and fluids. The selected material can be coated or impregnated with a therapeutic agent or material, such as an oligodynamic metal or an antimicrobial medium.

A fabric material, e.g., SPANDEX containing a mixture of LYCRA and NYLON may be superposed over cam fingers 11, duckbill seal 12, and instrument seal 13 to minimize the potential of piercing, penetrating, or tearing by the instrumentation.

In another embodiment (not shown), a septum valve having a preformed puncture or crossed slits or a similar valve that is biased inward to provide a fluid/gas seal both when an instrument is inserted therethrough and in the absence of an instrument, can be used instead of or in conjunction with duckbill seal 12.

It will be understood by those skilled in the art that various modifications and changes in form and detail may be made therein without departing from the scope and spirit of the present disclosure. Accordingly, modifications and changes in form and detail may be made therein without departing from the scope and spirit of the present disclosure.

What is claimed is:

1. A seal device, comprising:
   a seal housing defining a central axis, the seal housing including an inner wall and an outer wall, the inner wall defining an opening along the central axis;
   a rotatable head mounted to the seal housing;
   at least one finger pivotally mounted to the rotatable head; and
   a cam operably coupled to the rotatable head and the at least one finger such that direct engagement and rotation of the rotatable head by an operator causes rotation of the cam and the at least one finger to define an aperture dimensioned to receive a surgical instrument of a predetermined size, the at least one finger configured to reduce the amount by which the surgical instrument may be moved off-axis relative to the central axis.

2. The seal device of claim 1, further comprising an instrument seal for substantially sealing about the surgical instrument.

3. The seal device of claim 1, further comprising a zero-closure seal for providing a substantial seal in the absence of a surgical instrument.

4. The seal device of claim 1, wherein the seal device includes three fingers.

5. The seal device of claim 1, wherein the rotatable head includes indicia which provide and indication to a user of the appropriate size of an instrument that may be inserted therethrough.

6. The seal device of claim 5, wherein the indicia includes a window defined by the rotatable head through which numerical markings may be visible.

7. A seal device, comprising:
   a seal housing;
   a cam rotatably disposed within the seal housing;
   a head operably coupled to the cam; and
   at least one cam finger pivotably disposed within the seal housing and in mechanical communication with the cam, the at least one cam finger defining an aperture having a first diameter through the seal housing;
   wherein the cam is operably coupled to the head and the at least one cam finger such that rotation of the head by an operator results in rotation of the cam and the at least one finger, the at least one finger configured to maintain a second diameter through the seal housing, the second diameter being different from the first diameter to receive an instrument of a preselected size.

8. The seal device of claim 7, wherein the head includes indicia corresponding to a diameter of the aperture.

9. The seal device of claim 7, wherein the cam is configured for operation proximally of the seal housing.

10. The seal device of claim 7, wherein at least one seal member is associated with the seal device.

* * * * *